United States Patent

Fujiwara et al.

(10) Patent No.: US 8,900,602 B2
(45) Date of Patent: *Dec. 2, 2014

(54) DISINTEGRATING PARTICLE COMPOSITION AND ORALLY RAPIDLY DISINTEGRATING TABLET

(75) Inventors: Keiichi Fujiwara, Ibaraki (JP); Tadashi Fukami, Kamiichi-machi (JP); Haruka Koizumi, Kamiichi-machi (JP)

(73) Assignee: Fuji Chemical Industry Co., Ltd., Toyama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/389,874

(22) PCT Filed: Aug. 11, 2010

(86) PCT No.: PCT/JP2010/063602
§ 371 (c)(1),
(2), (4) Date: Feb. 10, 2012

(87) PCT Pub. No.: WO2011/019046
PCT Pub. Date: Feb. 17, 2011

(65) Prior Publication Data
US 2012/0165413 A1  Jun. 28, 2012

(30) Foreign Application Priority Data

Aug. 11, 2009 (JP) ................................ 2009-186648

(51) Int. Cl.
*A23L 1/48* (2006.01)
*A61K 47/26* (2006.01)
*A61K 9/20* (2006.01)
*A61K 31/5375* (2006.01)
*A61K 9/00* (2006.01)

(52) U.S. Cl.
CPC .............. *A61K 9/0056* (2013.01); *A61K 9/2018* (2013.01); *A61K 31/5375* (2013.01)
USPC ............ 424/400; 514/770; 514/769; 426/661

(58) Field of Classification Search
USPC ........................................................ 424/400
See application file for complete search history.

(56) References Cited

U.S. PATENT DOCUMENTS

| 2005/0106240 A1* | 5/2005 | Tanaka et al. ................. 424/464 |
| 2007/0275058 A1 | 11/2007 | Tanaka et al. |
| 2008/0206327 A1 | 8/2008 | Stroppolo et al. |

FOREIGN PATENT DOCUMENTS

| EP | 1 523 974 | 4/2005 | |
| JP | 10-120554 | 5/1998 | |
| JP | 11-310539 | 11/1999 | |
| JP | 2000/86537 | 3/2000 | |
| JP | 2005-139168 | 6/2005 | |
| JP | 2005-306770 | * 11/2005 | ............... 424/401 |
| JP | 2005/306770 | 11/2005 | |
| JP | 2009-114113 | 5/2009 | |
| WO | 2005/037254 | 4/2005 | |
| WO | 2005/37319 | 4/2005 | |
| WO | 2007/029376 | 3/2007 | |
| WO | 2007/29379 | 3/2007 | |

OTHER PUBLICATIONS

Translation of JP2005-306770 A. Inventors: Ishikawa, T. Published Nov. 4, 2005. Cited in IDS filed Feb. 10, 2012.*
International Preliminary Report on Patentability and Written Opinion issued Mar. 13, 2012 in International Application No. PCT/JP2010/063602, of which the present application is the national stage.
International Search Report issued Oct. 5, 2010 in International (PCT) Application No. PCT/JP2010/063602, of which the present application is the national stage.
Supplementary European Search Report issued Dec. 12, 2012 in corresponding European Patent Application No. 10808229.8.
English abstract of JP 2005-139168, Jun. 2, 2005.
English abstract of JP 2000-086537, Mar. 28, 2000.
English abstract of JP 2005-306770, Nov. 4, 2005.
English abstract of JP 10-120554, May 12, 1998.
English abstract of JP 2009-114113, May 28, 2009.
English abstract of JP 11-310539, Nov. 9, 1999.

* cited by examiner

*Primary Examiner* — Audrea Buckley
(74) *Attorney, Agent, or Firm* — Wenderoth, Lind & Ponack, L.L.P.

(57) ABSTRACT

Disclosed is an orally rapidly disintegrating tablet which has a good texture and taste in the oral cavity, such a sufficient hardness as not giving any worry of being chipped or dusted during production or transportation and good disintegrating properties in the oral cavity. The orally rapidly disintegrating tablet, which has a good texture and taste, an appropriate hardness, and good disintegrating properties, can be produced by using a composition, which is prepared by dispersing, by spray-drying, an inorganic excipient and starch(es) in complex particles composed of mannitol and xylitol, in an orally rapidly disintegrating tablet.

6 Claims, No Drawings

DISINTEGRATING PARTICLE COMPOSITION AND ORALLY RAPIDLY DISINTEGRATING TABLET

TECHNICAL FIELD

The present invention relates to a disintegrating particle composition which is prepared by dispersing mannitol, xylitol, inorganic excipient(s) and starch(es) in complex particles, and an orally rapidly disintegrating tablet comprising the disintegrating particle composition.

BACKGROUND ART

Orally rapidly disintegrating tablets have been developed as a form which is easy to be taken by patients, elderly people, children, etc. who have difficulty in swallowing drugs, or is easy to be taken without water. The orally rapidly disintegrating tablets should have such a sufficient hardness as not being chipped or dusted during production or transportation of tablets or opening, and in addition, it is required that a disintegration time in the oral cavity is within about 60 seconds and a texture and taste in the oral cavity has no problem. There are more problems to be solved in the orally rapidly disintegrating tablets compared to normal tablets. Specifically, a disintegration time and hardness are contradictory factors, and in general, disintegration times tend to be extended as molding pressures are increased for the purpose of the increase of hardness, and hardness tends to be decreased as molding pressures are decreased for the purpose of the shortening of disintegration times.

An orally rapidly disintegrating composition which is prepared by granulating an organic acid such as tartaric acid, a hydrogen carbonate salt of alkali metal such as sodium hydrogen carbonate, a network maintenance agent such as cornstarch or potato starch, a color protection agent such as mannitol or xylitol, followed by compressing to mold has been known (Patent Document 1). The composition becomes fizzy by the reaction of an organic acid with a carbonate salt under moisture condition in the oral cavity, and a drying process is required to prepare the composition in addition to the compression molding process.

An orally rapidly disintegrating formulation which is prepared by dry-blending hydroxypropylstarch, spray-dried D-mannitol, a physiologically active ingredient and anhydrous silicic acid, followed by compressing to mold has been known (Patent Document 2).

An orally rapidly disintegrating tablet comprising a pharmaceutical composition obtained by dispersing sugar and an inorganic compound in water and spray-drying (Patent Document 3), and a composition for an orally rapidly disintegrating tablet characterized by dispersing complex particles of sugar, a disintegrant and an inorganic substance in the presence of water (Patent Documents 4, 5, 6) have been known.

It has never been known that a disintegrating particle composition which is prepared by dispersing inorganic excipient(s) and starch(es) in complex particles which are composed of mannitol and xylitol, and an orally rapidly disintegrating tablet comprising the composition have better molding properties, hardness and disintegrating properties than those prepared by the conventional method.

[Patent document 1] JP-A-11-310539
[Patent document 2] JP-A-2005-306770
[Patent document 3] JP-A-2000-86537
[Patent document 4] WO 2005/37319 pamphlet
[Patent document 5] WO 2005/37254 pamphlet
[Patent document 6] WO 2007/29376 pamphlet

DISCLOSURE OF INVENTION

Problems to be Solved by the Invention

The present invention is directed to provide a disintegrating particle composition which is appropriate for an orally rapidly disintegrating tablet which have an improved texture and taste in the oral cavity, such a sufficient hardness as not giving any worry during production or transportation and good disintegrating properties in the oral cavity, compared to orally rapidly disintegrating tablets in the conventional art, and an orally rapidly disintegrating tablet comprising the disintegrating particle composition.

Means of Solving the Problems

According to extensive studies to achieve the above purpose, the present inventors have found a disintegrating particle composition, which is prepared by homogeneously dispersing inorganic excipient(s) and starch(es) in complex particles which are composed of mannitol and xylitol. The present inventors have also found an orally rapidly disintegrating tablet which has excellent disintegrating properties, such a sufficient hardness as not giving any worry during production or transportation and a sufficient texture and taste in the oral cavity, which is prepared by mixing the disintegrating particle composition together with an active ingredient, disintegrant(s), and ingredient(s) such as lubricant, excipient, binders which do not impair the effect of the present invention.

Specifically, the present invention is the following (1) to (11).

(1) A disintegrating particle composition, which is prepared by dispersing inorganic excipient(s) and starch(es) in complex particles which are composed of mannitol and xylitol, wherein
(a) the sum of mannitol and xylitol is 70 to 90 parts by weight;
(b) the inorganic excipient(s) are in the amount of 2 to 15 parts by weight;
(c) the starch(es) are in the amount of 5 to 25 parts by weight, and
the total amount of the ingredients (a), (b) and (c) is 100 parts by weight;

(2) A disintegrating particle composition, which is prepared by homogeneously dispersing inorganic excipient(s) and starch(es) in complex particles which are composed of mannitol and xylitol, wherein
(a) the sum of mannitol and xylitol is 70 to 90 parts by weight;
(b) the inorganic excipient(s) are in the amount of 2 to 15 parts by weight;
(c) the starch(es) are in the amount of 5 to 25 parts by weight, and
the total amount of the ingredients (a), (b) and (c) is 100 parts by weight;

(3) The composition of (2), wherein
(a) the sum of mannitol and xylitol is 75 to 85 parts by weight;
(b) the inorganic excipient(s) are in the amount of 3 to 9 parts by weight; and
(c) the starch(es) are in the amount of 10 to 15 parts by weight;

(4) The composition of (3), wherein the ratio by weight of mannitol to xylitol is 99:1 to 90:10;

(5) The composition of (3), wherein the ratio by weight of mannitol to xylitol is 99:1 to 95:5;

(6) The composition of any one of (1) to (5), wherein the inorganic excipient(s) are at least one or more agents selected from magnesium aluminometasilicate, magnesium aluminosilicate, anhydrous silicic acid, calcium silicate, calcium hydrogen phosphate, calcium carbonate or talc;

(7) The composition of any one of (1) to (5), wherein the starch(es) are at least one or more agents selected from potato starch, flour starch, sticky rice starch, sweet potato starch, tapioca starch, rice starch, cornstarch, waxy cornstarch or hydroxypropylstarch;

(8) A method for preparing the composition of any one of (1) to (7), comprising a step wherein a dispersion comprising the ingredients (a) to (c) is spray-dried;

(9) An orally rapidly disintegrating tablet, comprising 0.1 to 200 parts by weight of the active ingredient and 10 to 100 parts by weight or less of a disintegrant per 100 parts by weight of the composition of any one of (1) to (7),

(10) The orally rapidly disintegrating tablet of (9), wherein the disintegrant is potato starch, flour starch, sticky rice starch, sweet potato starch, tapioca starch, rice starch, cornstarch, waxy cornstarch, hydroxypropylstarch or crospovidone, and

(11) The orally rapidly disintegrating tablet of any one of (9) to (10), further comprising a lubricant, wherein the lubricant is externally added.

Effect of Invention

The orally rapidly disintegrating tablet comprising the orally rapidly disintegrating particle composition of the present invention is characterized by having such a sufficient hardness as not giving any worry during production or transportation and good disintegration times in the oral cavity and being able to prepare in simple steps. The orally rapidly disintegrating tablet may be also used in medicine or food which rapid disintegrating properties in the oral cavity are required.

BEST MODE FOR CARRYING OUT THE INVENTION

The disintegrating particle composition of the present invention is a spherical particulate composition which is prepared by dispersing inorganic excipient(s) and starch(es) in complex particles which are composed of mannitol and xylitol, preferably the composition wherein the dispersing is homogeneous dispersing. The "complex particles" composed of mannitol and xylitol refer to particles wherein xylitol is solid-dispersed in mannitol particles. The "dispersing in complex particles" is observed by SEM images (scanning electron micrograph), etc., preferably "homogeneously dispersing in complex particles". The "homogeneously dispersing in complex particles" refers to a state wherein each ingredient which is identifiable by SEM images, etc. is dispersed in smaller particle sizes close to primary particles than apparent particle sizes upon addition in complex particles. The apparent particle sizes refer to average particle sizes measured by a dry particle size distribution analyzer.

Among sugar, mannitol is easy to use, since it is stable as an excipient in that it is not hygroscopic, it is not colored by a reaction such as Maillard reaction and it is poorly reactive with agents, but it is disadvantageous in that its molding properties are bad. The disintegrating particle composition of the present invention has good molding properties and disintegrating properties as well as temporal stabilities by spray-drying or freeze-drying mannitol to granule or to prepare amorphous, or by solid-dissolving or solid-dispersing xylitol into mannitol to prepare a complex base. These factors are described in JP-A-2005-139168.

The average particle size of the disintegrating particle composition of the present invention may be 1 to 400 µm, preferably 5 to 300 µm, in view of preventing roughness in the oral cavity and disintegrating properties. In view of the disintegrating properties in the oral cavity, fluidity during preparation of tablet and loading properties, the more spherical the disintegrating particle composition of the present invention is, the more preferable it is, and the degree of sphericity is 0.7 or more, more preferably 0.8 or more. The degree of sphericity is calculated by ratios of minor axis/major axis in SEM images or optical microscope. The average particle size of the disintegrating particle composition of the present invention obtained above is measured by Laser Diffraction Particle Size Analyzer [HELOS & RODOS] of SYMPATEC, Inc., for example.

In the present invention, the inorganic excipient refers to an agent having high-specific surface areas which is insoluble or hardly soluble in water, and includes at least one or more agents selected from magnesium aluminometasilicate, magnesium aluminosilicate, anhydrous silicic acid, calcium silicate, magnesium silicate, aluminum silicate, calcium hydrogen phosphate, anhydrous calcium hydrogen phosphate, an agglomerated material of anhydrous calcium hydrogen phosphate, hydrotalcite, calcium phosphate, calcium carbonate, magnesium oxide, magnesium hydroxide, magnesium hydroxide-aluminium hydroxide co-precipitate, dried aluminum hydroxide gel, magnesium carbonate, calcium carbonate or talc. Preferable one is at least one or more agents selected from magnesium aluminometasilicate, magnesium aluminosilicate, anhydrous silicic acid, calcium silicate, calcium hydrogen phosphate, calcium carbonate or talc.

It is preferable that the inorganic excipient has high-specific surface areas in view of water-conducting properties or dispersibilities in complex particles, and BET-specific surface area is 20 to 500 $m^2/g$ and a preferable BET-specific surface area is 50 to 300 $m^2/g$. It is considered that one having high-specific surface areas improves permeabilities of water in granulated particles by water-conducting effects and disrupts granulated particles immediately in contact with water due to its aggregated structure of a few micrometers or less of primary particles. When an inorganic excipient with high-specific surface areas is used to compress and mold into a tablet form in the production of the granulated particles of the present invention, the inorganic excipient reduces the water content of sugar by adjusting concentrations of water in a tablet. Binding forces at junction points of disintegrating particle compositions proceed to reduce under humid conditions after opening by the adjusting effect. When the inorganic excipient is used, the granulation efficiency by spray may be improved and the yields of the disintegrating particle composition of the present invention may be improved.

In the present invention, the starch(es) are preferably those which are hardly soluble in water for the purpose of dispersing in complex particles, and include at least one or more agents selected from potato starch, flour starch, sticky rice starch, sweet potato starch, tapioca starch, rice starch, cornstarch, waxy cornstarch, pregelatinized starch, hydroxypropyl starch or sodium carboxymethyl starch. Preferable one is at least one or more agents selected from potato starch, flour starch, sticky rice starch, sweet potato starch, tapioca starch, rice starch, cornstarch, waxy cornstarch or hydroxypropylstarch.

Mannitol and starch(es) with 0.1 to 500 µm of the average particle size, preferably 1 to 200 µm of the average particle size, may be used for the purpose of preventing roughness in the oral cavity. The inorganic excipient(s) which are hardly soluble in water may be used in the average particle size of 0.1 to 60 μm, preferably 0.1 to 20 μm or less, for the purpose of the dispersion in the composition or the prevention of roughness in the oral cavity.

The blending amounts of each ingredient in the disintegrating particle composition of the present invention is 70 to 90 parts by weight of the sum of mannitol and xylitol, 2 to 15 parts by weight of the inorganic excipient(s) and 5 to 25 parts by weight of starch(es) per 100 parts by weight of the total amount of the ingredients (a) to (c), preferably 75 to 85 parts by weight of the sum of mannitol and xylitol, 3 to 9 parts by weight of the inorganic excipient(s) and 10 to 15 parts by weight of starch(es), further preferably 75 to 80 parts by weight of the sum of mannitol and xylitol, 4 to 8 parts by weight of the inorganic excipient(s) and 12 to 14 parts by weight of starch(es).

The complex particles of the present invention are composed of mannitol and xylitol, and the ratio by weight of mannitol and xylitol is 99:1 to 90:10, preferably 99:1 to 95:5, further preferably 99:1 to 97:3.

The static specific volume of the disintegrating particle composition of the present invention is preferably 1.5 to 4.0 ml/g, more preferably 1.5 to 3.5 ml/g, further preferably 1.5 to 2.5 ml/g. Such a static specific volume of the disintegrating particle composition can achieve smoothness during formulation due to ease of loading into mortar during molding tablet, and excellent tableting properties to provide homogeneous compression of tablet. The static specific volume may be measured in accordance with conventional methods.

The disintegrating particle composition of the present invention may comprise the following active ingredient and other ingredients to be blended without impairing disintegrating properties, if needed, and the blending amount of each ingredient is 0.01 to 200 parts by weight of the active ingredient, 10 to 100 parts by weight of a disintegrant and 0.1 to 100 parts by weight of other ingredients to be blended without impairing disintegrating properties per 100 parts by weight as the sum of mannitol, xylitol, inorganic excipient(s) and starch(es), preferably 0.1 to 100 parts by weight of the active ingredient, 10 to 50 parts by weight of a disintegrant and 0.1 to 50 parts by weight of other ingredients to be blended without impairing disintegrating properties per 100 parts by weight as the sum of mannitol, xylitol, inorganic excipient(s) and starch(es).

The disintegrating particle composition of the present invention may be usually prepared by any methods wherein each ingredient may be dispersed such as spraying methods including spray drying, tumbling granulation, agitation granulation, fluidized-bed granulation, freeze-drying methods. It is preferable that the composition is prepared by the spraying method wherein the ingredients are easy to be dispersed and spherical particles are easy to prepare. The disintegrating particle composition of the present invention may be prepared by the common spraying method in which mannitol, xylitol, inorganic excipient(s) and starch(es) are dispersed in an aqueous solvent and the dispersion is spray dried. More specifically, mannitol, xylitol, inorganic excipient(s) and starch(es) are added to an aqueous solvent to prepare a dispersion in the method, and a dosing order of the ingredients is not specified. In order to completely dissolve the ingredients, it is preferable that mannitol and xylitol are preliminarily dissolved or dispersed in an aqueous solvent, followed by inorganic excipient(s), starch(es) are homogeneously dispersed to prepare. After that, the dispersion may be spray-dried to give the disintegrating particle composition of the present invention. When the active ingredient, an agent controlling the influence of the active ingredient on the molding properties or disintegrating properties, and the following other ingredients to be blended without impairing disintegrating properties are blended, these agents are added to spray drying during the preparation of the dispersion.

The above aqueous solvent may be any solvent which do not affect properties of the disintegrating particle composition and may be acceptable for pharmaceuticals or foods, and includes water, ethanol, acetone, for example. The dispersion may be prepared according to the known method which includes conventional stirring, colloid milling, high-pressure homogenizing, ultrasonic irradiation, wet-type atomizing, for example, and may be any methods which may highly disperse particles in an aqueous dispersion. The concentration of the composition in the dispersion may be any concentration to the extent that the dispersion can be spray-dried which may vary depending on the viscosity of the dispersion, specifically 5 to 50% by weight, preferably 10 to 45% by weight.

Conditions of spray-drying are not limited, but a preferable spray-drying machine is a disk or nozzle type spray-drying machine. The temperature in the spray-drying is preferably about 120 to 220° C. at inlet temperature, and about 80 to 130° C. at outlet temperature. The concentration of solid materials in the aqueous dispersion in the spray drying may be any concentrations which spray drying may be carried out. The particle size of the disintegrating particle composition may be optionally controlled by concentrations of an aqueous solution or aqueous dispersion, spray-drying methods, drying conditions.

The "orally rapidly disintegrating tablet" in the present invention refers to a tablet which may rapidly disintegrate in the oral cavity, for example within 60 seconds, preferably within 40 seconds, further preferably within 30 seconds. The disintegration time in the oral cavity herein is time needed in the following conditions of the orally rapidly disintegrating tablet or Example methods. The disintegration time in the oral cavity differs between tablets depending on the size or figure of tablet, which is also included in the present invention.

In the present invention, the "texture" which does not generate discomfort in the oral cavity refers to the feeling without causing mealy texture or muddy smell which does not cause a feeling wherein blending materials just absorb water to swell and a tablet does not disintegrate, i.e. without fluffy feelings, and the "taste" which does not generate discomfort in the oral cavity refers to the feeling without tartness (i.e., sourness), bitter taste, hard taste derived from starting materials.

The orally rapidly disintegrating tablet of the present invention may comprise an active ingredient, a disintegrant and other ingredients to be blended without impairing disintegrating properties, if needed. The blending ratio of each ingredient is 0.01 to 200 parts by weight of an active ingredient, 10 to 100 parts by weight of a disintegrant and 0.1 to 100 parts by weight of other ingredients to be blended without impairing disintegrating properties per 100 parts by weight of the disintegrating particle composition, preferably 0.1 to 100 parts by weight of an active ingredient, 10 to 50 parts by weight of a disintegrant and 0.1 to 50 parts by weight of other ingredients to be blended without impairing disintegrating properties per 100 parts by weight of the total amount of mannitol, xylitol, inorganic excipient(s) and starch(es).

In the present invention, the disintegrant is, for example, one or more agents selected from adipic acid, alginic acid, sodium alginate, pregelatinized starch, erythritol, fructose, sodium carboxymethyl starch, carmellose, carmellose calcium, carmellose sodium, aqueous silicon dioxide, agar, xylitol, guar gum, calcium citrate, croscarmellose sodium, crospovidone, synthetic aluminum silicate, magnesium aluminosilicate, low-substituted hydroxypropylcellulose, crystalline cellulose, crystalline cellulose carmellose sodium, sticky rice starch, potato starch, flour starch, sweet potato starch, tapioca starch, rice starch, cornstarch, waxy cornstarch, cellulose acetate phthalate, dioctyl sodium sulfosuccinate, sucrose fatty acid ester, magnesium hydroxide-aluminium hydroxide co-precipitate, calcium stearate, polyoxyl stearate, sorbitan sesquioleate, gelatin, shellac, sorbitol, sorbitan fatty acid ester, talc, sodium hydrogen carbonate, magnesium carbonate, precipitated calcium carbonate, dextrin, sodium dehydroacetate, cornstarch, tragacanth, trehalose, lactose, maltose, saccharose, hydrotalcite, honey, palatinit, palatinose, potato starch, hydroxyethylmethylcellulose, hydroxypropyl starch, hydroxypropylcellulose, glucose, bentonite, partially pregelatinized starch, monosodium fumarate, polyethylene glycol, polyoxyethylene hardened castor oil, polyoxyethylene polyoxypropylene glycol, polysorbate, polyvinyl acetal diethylamino acetate, polyvinylpyrrolidone, maltitol, D-mannitol, anhydrous citric acid, anhydrous silicic acid, magnesium aluminometasilicate, methylcellulose, glycerin monostearate or sodium lauryl sulfate, and any one of them may be used alone and two or more of them may be mixed. Preferable one is crospovidone, hydroxypropyl starch, sticky rice starch, potato starch, flour starch, sweet potato starch, tapioca starch, rice starch, cornstarch or waxy cornstarch.

In the present invention, the active ingredient refers to an active principle for medicament or a nutrient component in food. The active ingredient may be added alone, or in the sustained releasable form or the coated or granulated form of the active ingredient so as to mask bitter taste. The coating processing includes a method spray drying the active ingredient and agents such as an insoluble polymer, stomach-soluble polymer, enteric polymer, a method mixing the active ingredient with methylcellulose and mannitol.

The active ingredient includes central nervous system agents, peripheral nervous system agents, agents affecting sensory organs, agents affecting circulatory organs, agents affecting respiratory organs, agents affecting digestive organs, hormonal agents, agents affecting genitourinary apparatus, medicaments affecting other organs, vitamin preparations, revitalizers, agents for blood or body fluid, other metabolized drugs, cellular stimulants, antineoplastic agents, radioactive agents, anti-allergic agents, other medicaments for tissue cellular functions, natural medicine, Chinese medicine, other natural medicine and medicine based on Chinese medicine prescription, antibiotic agents, chemotherapeutic agents, biological preparations, agents against parasitic animals, other medicine against pathogenic organism, dispensing agents, diagnostic agents, agents for public health, extracorporeal diagnostic agents, other agents not mainly intended for treatment, alkaloidal narcotics (natural narcotics), and non-alkaloidal narcotics (Drugs in Japan 2008, Jihou, Inc.), but is not limited thereto.

Hypnosedatives or anti-anxiety agents among the central nervous system agents include alprazolam, estazoram, dexmedetomidine hydrochloride, rilmazafone hydrochloride, oxazolam, quazepam, tandospirone citrate, cloxazolam, clorazepate dipotassium, chlordiazepoxide, diazepam, potassium bromide, calcium bromide, sodium bromide, zolpidem tartrate, secobarbital sodium, zopiclone, tofisopam, triazolam, triclofos sodium, nitrazepam, nimetazepam, passiflora extract, barbital, haloxazolam, phenobarbital, prazepam, fludiazepam, flutazolam, flutoprazepam, flunitrazepam, flurazepam hydrochloride, brotizolam, bromazepam, bromovalerylurea, pentobarbital, chloral hydrate, midazolam, mexazolam, medazepam, ethyl loflazepate, lorazepam, lormetazepam.

Antiepileptic agents include acetylpheneturide, gabapentin, carbamazepine, clonazepam, clobazam, sultiame, zonisamide, trimethadione, sodium valproate, phenytoin, primidone.

Antipyretics, analgesics or antiphlogistics include actarit, aspirin, acetaminophen, ampiroxicam, ibuprofen, indomethacin, indomethacinfarnesyl, ethenzamide, etodolac, epirizole, emorfazone, tramadol hydrochloride, buprenorphine hydrochloride, oxaprozin, ketoprofen, sodium salicylate, zaltoprofen, diclofenac sodium, sulindac, sulpyrine hydrate, celecoxib, tiaprofenic acid, tiaramide hydrochloride, tenoxicam, naproxen, bucolome, pentazocin, mefenamic acid, meloxicam, mofezolac, loxoprofen sodium hydrate.

Antiparkinson agents include amantadine hydrochloride, selegiline hydrochloride, talipexole hydrochloride, piroheptine hydrochloride, pramipexole hydrochloride hydrate, mazaticol hydrochloride, metixene hydrochloride, entacapone, cabergoline, trihexyphenidyl hydrochloride, droxidopa, biperiden, bromocriptine mesilate, pergolide mesilate, levodopa.

Psychoneurotic agents include amitriptyline hydrochloride, amoxan, aripiprazole, imipramine hydrochloride, etizolam, sultopride hydrochloride, sertraline hydrochloride, trazodone hydrochloride, paroxetine hydrochloride hydrate, floropipamide hydrochloride, perospirone hydrochloride hydrate, mianserin hydrochloride, milnacipran hydrochloride, methylphenidate hydrochloride, mosapramine hydrochloride, moperone hydrochloride, lofepramine hydrochroride, oxypertine, olanzapine, carpipramine, clocapramine hydrochloride hydrate, clotiazepam, clomipramine hydrochloride chlorpromazine, spiperone, sulpiride, zotepine, lithium carbonate, timiperone, haloperidol decanoate, nemonapride, nortriptyline hydrochloride, haloperidol, hydroxyzine hydrochloride, hydroxyzine pamoate, pimozide, quetiapine fumarate, fluphenazine, prochlorperazine, propericiazine, bromperidol, perphenazine, maprotiline hydrochloride, setiptiline maleate, trifluoperazine maleate, trimipramine maleate, fluvoxamine maleate, modafinil, risperidone, levomepromazine.

Other central nervous system agents include tiapride hydrochloride, donepezil hydrochloride, taltirelin hydrate, terguride, mazindol, riluzole.

Regional anesthetics among the peripheral nervous system agents include ethyl aminobenzoate, bupivacaine hydrochloride, ropivacaine hydrochloride hydrate, oxethazaine, procaine hydrochloride, mepivacaine hydrochloride, lidocain.

Autonomic agents include ambenonium chloride, oxapium iodide, distigmine bromide, propantheline bromide, mepenzolate bromide.

Spasmolytic agents include afloqualone, eperisone hydrochloride, piperidolate hydrochloride, tizanidine hydrochloride, timepidium bromide hydrate, tolperisone hydrochloride, baclofen, papaverine hydrochloride, butylscopolamine bromide, butropium bromide, flopropione, N-methylscopolamine methylsulfate.

Otological agents of the agents affecting sensory organs include amlexanox, lomefloxacin hydrochloride, ofloxacin, chloramphenicol. Antimotionsickness agents include isoproterenol hydrochloride, diphenidol hydrochloride, betahistine mesylate.

Cardiotonic agents among the agents affecting circulatory organs include aminophylline hydrate, etilefrine hydrochloride, isoproterenol hydrochloride, choline theophylline, digitoxin, digoxin, denopamine, pimobendan, proxyphylline, vesnarinone, methyldigoxin, ubidecarenone.

Antiarrhythmic agents include ajimarine, acebutolol hydrochloride, atenolol, alprenolol hydrochloride, arotinolol hydrochloride, aprindine hydrochloride, amiodarone hydrochloride, sotalol hydrochloride, pilsicainide hydrochloride, propafenone hydrochloride, bepridil hydrochloride, oxprenolol hydrochloride, carteolol hydrochloride, quinidine sulfate hydrate, cibenzoline succinate, flecainide acetate, disopyramide, nadolol, pindolol, bufetolol hydrochloride, bisoprolol fumarate, procainamide hydrochloride, propranolol hydrochloride, verapamil hydrochloride, mexiletine hydrochloride.

Diuretics include azosemide, chlorthalidone, spironolactone, torasemide, triamterene, trichlormethiazide, hydrochlorothiazide, piretanide, bumetanide, furosemide, benzylhydrochlorothiazide, mefruside, mozavaptan hydrochloride.

Hypotensive agents include azelnidipine, alacepril, aranidipine, indapamide, amosulalol hydrochloride, imidapril hydrochloride, efonidipine hydrochloride, quinapril hydrochloride, celiprolol hydrochloride, tilisolol hydrochloride, temocapril hydrochloride, terazosin hydrochloride, delapril hydrochloride, barnidipine hydrochloride, prazosin hydrochloride, betaxolol hydrochloride, benazepril hydrochloride, bevantolol hydrochloride, manidipine hydrochloride, labetalol hydrochloride, olmesartan medoxomil, cadralazine, captopril, carteolol hydrochloride, carvedilol, candesartan cilexetil, guanabenz acetate, clonidine hydrochloride, cilazapril, cilnidipine, telmisartan, todralazine hydrochloride hydrate, trandolapril, tripamide, nicardipine hydrochloride, nipradilol, nilvadipine, valsartan, hydralazine hydrochloride, pindolol, felodipine, budralazine, bunazosin hydrochloride, propranolol hydrochloride, perindopril erbumine, penbutolol sulfate, enalapril maleate, bopindolol malonate, doxazosin mesilate, meticrane, methyl-DOPA hydrate, metoprolol tartrate, lisinopril hydrate, rescinnamine, reserpine, losartan potassium.

Vasoconstrictive agents include rizatriptan benzoate, midodrine hydrochloride, dihydroergotamine mesylate, eletriptan hydrobromide, sumatriptan, zolmitriptan.

Vasodilators include isosorbide mononitrate, inositol hexanicotinate, isoxsuprine hydrochloride, dipyridamole, isosorbide dinitrate, dilazep hydrochloride hydrate, diltiazem hydrochloride, trapidil, trimetazidine hydrochloride, nicorandil, nisoldipine, nitrendipine, nitroglycerin, nifedipine, amlodipine besylate, benidipine hydrochloride, hepronicate, verapamil hydrochloride.

Antihyperlipidemic agents include atorvastatincalcium hydrate, ezetimibe, elastase ES, clinofibrate, clofibrate, colestimide, simvastatin, soysterol, sodium dextran sulfate, nicomol, niceritrol, pitavastatin calcium, fenofibrate, pravastatin sodium, fluvastatin sodium, probucol, bezafibrate, polyenephosphatidylcholine, rosuvastatin calcium.

Other agents affecting circulatory organs include ifenprodil tartrate, indomethacin, sevelamer hydrochloride, fasudil hydrochloride hydrate, lomerizine hydrochloride, gamma-aminobutanoic acid, dihydroergotoxine mesylate, tocopherolnicotinic acid ester, nicergoline, bosentan hydrate, meclofenoxate hydrochloride, amezinium methyl sulfate.

Antitussive agents among the agents affecting respiratory organs include ephedrine hydrochloride, clofedanol hydrochloride, cloperastine, dimemorfan phosphate, dextromethorphan hydrobromide hydrate, pentoxyverine citrate, benproperine phosphate.

Expectorant agents include L-ethylcysteine hydrochloride, L-methylcysteine hydrochloride, L-carbocysteine, ambroxol hydrochloride, fudosteine, bromhexine hydrochloride.

Antitussive expectorant agents include eprazinone hydrochloride, guaifenesin, codeine phosphate hydrate, tipepidine hibenzate.

Bronchodilator agents include aminophylline hydrate, isoproterenol hydrochloride, clenbuterol hydrochloride, mabuterol hydrochloride, methoxyphenamine hydrochloride, orciprenaline sulfate, salbutamol sulfate, fenoterol hydrobromide, tulobuterol, theophylline, terbutaline sulfate, trimetoquinol hydrochloride hydrate, procaterol hydrochloride hydrate, formoterol fumarate hydrate.

Oral rinse includes azulene sodium sulfonate.

Antidiarrheals or antiflatulents among the agents affecting digestive organs include loperamide hydrochloride, dimethicone, resistant lactobacillus preparation, bifidobacteria preparation, berberine chloride hydrate, preparation for butyric acid bacteria.

Agents for peptic ulcer include azulene sodium sulfonate, aldioxa, benexate hydrochloride betadex, omeprazole, ornoprostil, gefarnate, cimetidine, sucralfate hydrate, sulpiride, cetraxate hydrochloride, sofalcone, teprenone, troxipide, nizatidine, pirenzepine hydrochloride hydrate, famotidine, plaunotol, proglumide, polaprezinc, irsogladine maleate, misoprostol, methylmethioninesulfonium chloride, ranitidine hydrochloride, lafutidine, sodium rabeprazole, lansoprazole, clebopride malate, rebamipide, roxatidine acetate hydrochloride.

Acid suppressants include magnesium oxide, magnesium hydroxide, sodium hydrogen carbonate, precipitated calcium carbonate, magnesium aluminometasilicate.

Laxatives include senna extract, sennoside, sodium picosulfate hydrate.

Choleretic agents include anetholtrithione, ursodeoxycholic acid, trepibutone, nicotinic acid, naphthylacetic acid.

Other agents affecting digestive organs include Mallotus japonicus extract, azulene sodium sulfonate, cetylpyridinium chloride, dequalinium chloride, azasetron hydrochloride, itopride hydrochloride, indisetron hydrochloride, granisetron hydrochloride, cevimeline hydrochloride hydrate, tropisetron hdyrochloride, ramosetron hydrochloride, ondansetron, kitasamycin acetate, mosapride citrate, domiphen bromide, dexamethasone, trimebutine maleate, domperidone, pilocarpine hydrochloride, polycarbophil calcium, mesalazine, metoclopramide.

Salivary gland hormone preparations or thyroid or parathyroid hormonal agents include dried thyroid, thiamazole, propylthiouracil, liothyronine sodium, levothyroxine sodium hydrate.

Anabolic steroids include mestanolone, methenolone.

Adrenal hormonal agents include cortisone acetate, fludrocortisone acetate, dexamethasone, triamcinolone, hydrocortisone, prednisolone, betamesone, methylprednisolone.

Androgenic hormonal agents include methyl testosterone.

Estrogenic hormonal and progestational hormonal agents include allylestrenol, estriol, ethinyl estradiol, chlormadinone acetate, conjugated estrogen, medroxyprogesterone acetate, dydrogesterone, norethisterone, pregnanediol, fosfestrol.

Other hormonal agents include kallidinogenase, clomiphene citrate, cyclophenyl, danazol, trilostane, finasteride.

Agents affecting reproductive tract among the agents affecting genitourinary apparatus include estriol, clotrimazole, chloramphenicol, tinidazole, metronidazole.

Oxytocics include methylergometrine maleate.

Contraceptive agents include ethinyl estradiol norethisterone, ethinyl estradiol levonorgestrel, desogestrel ethinyl estradiol.

Agents for hemorrhoidal disease include venous plexus extract, tribenoside, bromelain tocopherol acetate, melilot extract.

Other agents affecting genitourinary apparatus include imidafenacin, Quercus salicina extract, oxybutynin hydrochloride, vardenafil hydrochloride hydrate, propiverine hydrochloride, sildenafil citrate, solifenacin succinate, tolterodine tartrate, silodosin, cernitin pollen extract, tamsulosin hydrochloride, naftopidil, flavoxate hydrochloride, ritodrine hydrochloride.

Other agents for each organ include gamma-oryzanol, cepharanthine.

Vitamin A and D preparations among the vitamin preparations include alfacalcidol, calcitriol, vitamin A, falecalcitriol.

Vitamin B1 preparations include dicethiamine hydrochloride, octothiamine, thiamine disulfide, bisbentiamine, fursultiamine, benfotiamine.

Vitamin B preparations include cobamamide, nicotinic acid, pantethine, hydroxocobalamin acetate, pyridoxine hydrochloride, flavin adenine dinucleotide, mecobalamin, folic acid, riboflavin butyrate, pyridoxal phosphate.

Vitamin C preparations include ascorbic acid, and vitamin E preparations include tocopherol calcium succinate, tocopherol acetate.

Vitamin K preparations include phytonadione, menatetrenone.

Other vitamin preparations include astaxanthin, fucoxanthin, lutein.

Calcium preparations among the revitalizers include calcium L-aspartate, calcium lactate hydrate.

Mineral preparations include potassium L-aspartate, potassium chloride, sodium ferrous citrate, potassium gluconate, iodine lecithin, iron sulfate hydrate.

Hemostatic agents among the agents for blood or body fluid include carbazochrome sodium sulfonate hydrate, tranexamic acid, adrenochrome monoaminoguanidine mesilate.

Agents for inhibiting blood coagulation include warfarin potassium.

Other agents for blood or body fluid include aspirin, ethyl icosapentate, sarpogrelate hydrochloride, cilostazol, ticlopidine hydrochloride, beraprost sodium, limaprost alfadex, clopidogrel sulfate.

Agents for liver disorders among the other metabolized drugs include liver hydrolysate, diisopylamine dichloroacetate, tiopronin, protoporphyrin disodium, malotilate.

Detoxifying agents include calcium disodium edetate, glutathione, sodium hydrogen carbonate, calcium folinate.

Arthrifuges include allopurinol, colchicine, probenecid, benzbromarone.

Enzyme preparations include semi-alkaline proteinase, serrapeptase, pronase, bromelain, lysozyme hydrochloride.

Diabetes drugs include acarbose, acetohexamide, pioglitazone hydrochloride, buformin hydrochloride, gliclazide, glyclopyramide, glybuzole, glibenclamide, glimepiride, chlorpropamide, tolbutamide, nateglinide, voglibose, miglitol, mitiglinide calcium hydrate, metformin hydrochloride.

Other metabolized drugs include azathioprine, adenosine triphosphate disodium salt, alendronate sodium hydrate, inosine pranobex, ipriflavone, etidronate disodium, epalrestat, everolimus, L-cysteine, levocarnitine chloride, raloxifene hydrochloride, camostat mesylate, cyclosporin, tacrolimus, mizoribine, methotrexate, sodium resedronate hydrate, leflunomide.

Cellular stimulants include adenine.

Antineoplastic agents include cyclophosphamide hydrate, melphalan, estramustine phosphate sodium, capecitabine, carmofur, tegafur, fluorouracil, methotrexate, fludarabine phosphate, etoposide, aceglatone, anastrozole, exemestane, fadrozole hydrochloride hydrate, tamoxifen citrate, toremifene citrate, tamibarotene, gefitinib, tamibarotene, bicalutamide, flutamide, procarbazine hydrochloride, imatinib mesylate, letrozole.

Anti-allergic agents include alimemazine, triprolidine hydrochloride, clemastine fumarate, chlorpheniramine maleate, diphenhydramine hydrochloride, cyproheptadine hydrochloride hydrate, promethazine hydrochloride, homochlorcyclizine hydrochloride, mequitazine, auranofin, bucillamine, amlexanox, ibudilast, ebastine, azelastine hydrochloride, epinastine hydrochloride, ozagrel hydrochloride, olopatadine hydrochloride, cetirizine hydrochloride, fexofenadine hydrochloride, oxatomide, ketotifen fumarate, zafirlukast, seratrodast, splatast tosilate, tranilast, emedastine difumarate, pranlukast hydrate, bepotastine besylate, pemirolast potassium, montelukast sodium, ramatroban, repirinast, loratadine.

Antibiotic agents include vancomycin hydrochloride, amoxicillin hydrate, cephalexin, cefaclor, cefixime, cefcapene pivoxil hydrochloride hydrate, cefdinir, cefteram pivoxil, cefpodoxime proxetil, azithromycin, enoxacin, clarithromycin, ciclacillin, josamycin, roxithromycin, levofloxacin.

Synthetic antibacterials include moxifloxacin hydrochloride, lomefloxacin hydrochloride, ofloxacin, ciprofloxacin, nalidixic acid, norfloxacin, pipemidic acid hydrate, fleroxacin.

Antivirus agents include aciclovir, adefovir pivoxil, efavirenz, emtricitabine, valaciclovir hydrochloride, entecavir hydrate, zanamivir hydrate, sanilvudin, didanosine, zidovudine, nevirapine, palivizumab, fosamprenavir calcium, saquinavir mesylate, delavirdine mesylate, lamivudine, ritonavir, ribavirin, abacavir sulfate, oseltamivir phosphate, lopinavir• ritonavir.

Other chemotherapeutic agents include itraconazole, terbinafine hydrochloride, furconazole.

Other effective ingredients may be, for example, one or more agents selected from the group consisting of deoxyribonucleic acid and a salt thereof, an adenylic acid derivative including adenosine triphosphate, adenosine monophosphate and a salt thereof, ribonucleic acid and a salt thereof, a nucleic acid-related material including guanine, xanthine and a derivative thereof and a salt thereof; an animal-derived extract including deproteinized blood serum extract, splenic extract, placental extract, cock's comb extract, royal jelly; a microbially-derived extract including yeast extract, lactic bacterium extract, bifidus extract, ganoderma lucidum extract; a plant-derived extract including carrot extract, Swertia japonica extract, rosemary extract, Phellodendoron amurense Ruprecht extract, garlic extract, aloe extract, salvia extract, arnica extract, chamomilla recutita extract, Japanese white birch extract, Hypericaceae extract, eucalyptus extract, soapberry extract, Inula britannica extract, Spatholobus suberectus extract, Cassia mimosoides extract, Morus alba extract, dong quai extract, adders-wort extract, Sophora Angustifolia extract, Crataegi fructus extract, white lily extract, hop extract, polyantha extract, Coix Lachryma-Jobi extract, loofa extract, Cnidium Officinale extract, blueberry extract, haematococcus extract, Pfaffia extract, ginkgo leaf extract, Asian ginseng extract, Hinokitiol, cepharanthine; α- or γ-linolenic acid, eicosapentaenoic acid, succinic acid, estradiol, glycolic acid, lactic acid, malic acid, citric acid, salicylic acid, glycyrrhizinic acid, glycyrrhetinic acid, phenylbutazone, allantoin, guaiazulene, ε-aminocaproic acid, hyaluronic acid, chondroitin, chondroitin sulfate, dermatan sulfate, heparan sulfate, heparin, keratan sulfate, cysteine and a derivative thereof and a salt thereof; collagen, elastin, keratin, deep seawater, papaya powder, zinc, DHA, glutathione, flavonoid, polyphenol, tannin, ellagic acid, nucleic acids, Chinese herbs, seaweeds, inorganic substances, and a mixture thereof.

When the active ingredient has a bitter taste or is needed to be released in the gastrointestinal tract may be used, the ingredient treated by known method such as coating may be used. For example, the active ingredient may be coated by the method of JP-A-11-263723, i.e, spray-drying fluidized-bed granulation, agitation granulation, or kneading granulation of the active ingredient with an easily soluble agent including xylitol, sorbitol, sucrose, an aqueous binder including polyvinylpyrrolidone, pullulan, hydroxypropylcellulose, hydroxypropyl methylcellulose, gum arabic, gelatin, and mannitol, lactose or mannose. It may be also coated by the method of JP-A-2002-275054, i.e., coating of the active ingredient with a gelling agent, a binder and sugar alcohol.

If hard taste, acid taste or bitter taste derived from starting materials may be suppressed by seasoning or flavoring, acidulant (e.g., citric acid, tartaric acid, malic acid, ascorbic acid, etc.), sweetening agent (e.g., sodium saccharin, dipotassium glycyrrhizinate, aspartame, stevia, thaumatin, etc.), flavoring substance, perfume (e.g., various fruit perfumes containing lemon oil, orange oil or strawberry, and yoghurt, mint, menthol, etc.) may be blended.

The other ingredients to be blended without impairing disintegrating properties may be any agents which are generally acceptable as a phamaceutical additive, and include, for example, acidulant, sweetener, flavoring substance, perfume, colorant, surfactant, excipient, binder, stabilizing agent, blowing agent.

The lubricant used in the present invention includes, for example, gum arabic powder, cacao butter, carnauba wax, carmellosecalcium, carmellosesodium, caropeptide, aqueous silicon dioxide, dried aluminum hydroxide gel, glycerin, magnesium silicate, light anhydrous silicic acid, light liquid paraffin, crystalline cellulose, hardened oil, synthetic aluminum silicate, sesame oil, flour starch, white beeswax, magnesium oxide, dimethyl polysiloxane, potassium sodium tartrate, sucrose fatty acid ester, glycerin fatty acid ester, silicon resin, aluminum hydroxide gel, stearyl alcohol, stearic acid, aluminum stearate, calcium stearate, polyoxyl stearate, magnesium stearate, cetanol, gelatin, talc, magnesium carbonate, precipitated calcium carbonate, cornstarch, lactose, hard fat, saccharose, potato starch, hydroxypropylcellulose, fumaric acid, sodium stearyl fumarate, polyethylene glycol, polyoxyethylene polyoxypropylene glycol, polysorbate, beeswax, magnesium aluminometasilicate, methylcellulose, Japan wax, glycerin monostearate, sodium lauryl sulfate, calcium sulfate, magnesium sulfate, liquid paraffin, phosphoric acid. Preferable one includes stearic acid, magnesium stearate, calcium stearate, sucrose fatty acid ester, polyethylene glycol, sodium stearyl fumarate or talc.

The orally rapidly disintegrating tablet of the present invention may be prepared by mixing the disintegrating particle composition with additives of at least one or more agents selected from lubricant, excipient, disintegrating aid and/or binding aid, an active ingredient, and other ingredients which can be blended in medicine, followed by compressing to mold. The compression molding is preferably carried out by a direct tableting method, in which the tableting pressure is usually 200 to 2000 kgf, preferably 250 to 1600 kgf, more preferably 250 to 1200 kgf, but varies according to the tablet sizes.

The orally rapidly disintegrating tablet of the present invention may be also prepared by wet-granulating at least one or more agents selected from the disintegrating particle composition, a disintegrant, the active ingredient or a binder, and the active ingredient, followed by compressing to mold. The wet-granulation includes spray drying, fluidized-bed granulation drying, agitation granulation or wet-extrusion granulation. The orally rapidly disintegrating tablet may also obtain the desired hardness or disintegrating properties by aging such as warming and/or humidifying according to the conventional method after compression molding.

In the preparation of the orally rapidly disintegrating tablet of the present invention, lubricant may be mixed with other ingredients, followed by compressing to mold, as mentioned above, but the tablet may be also prepared by a method (i.e., external lubrication) wherein lubricant is preliminarily applied to the surface of pestle and wall surface of mortar in a compression molding machine without mixing with other ingredients and a compression molding is carried out. By this method, the orally rapidly disintegrating tablet may obtain the desired hardness and disintegrating properties. The method applying lubricant to pestle and mortar may be carried out according to the conventional known methods and by using conventional machines.

The orally rapidly disintegrating tablet of the present invention has usually 20 to 200N, preferably 30 to 100N, of hardness. The tableting pressure varies according to the tablet sizes, but for example, the tablet has 30 to 150N of hardness when the tableting pressure is 100 to 1200 kgf, and the tablet has 30 to 80N of hardness when the tableting pressure is 100 to 1000 kgf, in case that 200 mg of tablet is tableted by using pestle with 8 mm of diameter.

The orally rapidly disintegrating tablet of the present invention may be also used as a solid preparation other than tablets intended for rapid disintegrating properties (e.g., a chewable tablet). The orally rapidly disintegrating tablet of the present invention may be also used as food such as healthy food or food for specified health uses, pet food or feedstuff, agrichemical, as well as medicine, due to rapid disintegrating properties by a small amount of water.

EXAMPLES

The present invention is illustrated by Examples as follows, but the scope of the present invention is not intended to be limited thereto.

Each tablet obtained in each Example was evaluated in the following manner.
[Disintegration Time in the Oral Cavity]
The time for a tablet to completely disintegrate on the tongue in the oral cavity (n=6 per a tablet) was measured for to 8 subjects, of which the average time provided the disintegration time in the oral cavity.
[Sensory Test]
A tablet was naturally disintegrated on the tongue in the oral cavity for 5 subjects. After that, a questionnaire about texture and taste was carried out.
[Hardness of Tablet]
It was measured by using Load-cell type tablet hardness tester [PC-30, manufactured by OKADA SEIKO CO., LTD.].
[Tableting Difficulties]
The mortar and pestle of a tableting machine and a tablet after tableting were observed, and sticking and capping, adherence and weight variation were analyzed.

Reference Example 1

Preparation of Masking Particles

Mosapride citrate was used as a bitter-tasting active ingredient to prepare masking particles according to the method of WO2005/55989. Specifically, 10 parts by weight of water was sprayed into 21 parts by weight of mosapride citrate 2 hydrate, 20 parts by weight of methylcellulose and 59 parts by weight of D-mannitol to be granuled by an agitation granulation machine, dried at 80° C. overnight, and filtered by 32 mesh sieve to prepare a masking particle.

Mosapride citrate was manufactured by Dainippon Sumitomo Pharma Co., Ltd., and Metolose SM-25 (2.53 mm$^2$/S of viscosity (2% aqueous viscosity at 20° C. (Japanese Pharmacopoeia)) manufactured by Shin-Etsu Chemical Co., Ltd. was used as methylcellulose and Mannite P manufactured by Mitsubishi Foodtech Co., Ltd. was used as mannitol.

Examples 1-3

Preparation of Disintegrating Particle Compositions

The ingredients of the prescriptions of Table 1 were homogeneously dispersed by water so as to be 35 parts by weight per 100 parts by weight of the entire dispersion, followed by spray-dried by using a spray drying machine (type L-8, manufactured by Ohkawara Kakohki Co., Ltd.) with 80° C. of the outlet temperature to give a fluid white spherical granulated particle.

TABLE 1

|  | Mannitol | Xylitol | Calcium silicate | Magnesium aluminometasilicate | Cornstarch | Rice starch | HPS | L-HPC |
|---|---|---|---|---|---|---|---|---|
| Example 1 | 78 | 2 | 6 | 6 | 9 |  | 5 | 5 |
| Example 2 | 78 | 2 | 6 | 6 | 9 | 5 |  |  |
| Example 3 | 78 | 2 |  | 6 |  |  | 5 | 9 |

(Unit: parts by weight)

HPS refers to hydroxypropylstarch.

L-HPC refers to low-substituted hydroxypropylcellulose.

Xylite XC manufactured by Mitsubishi Foodtech Co., Ltd. was used as xylitol, FlowLite RE manufactured by Eisai Food & Chemical Co., Ltd. was used as calcium silicate, Neusilin UFL2 ® manufactured by Fuji Chemical Industry Co., Ltd. was used as magnesium aluminometasilicate. Cornstarch W manufactured by Nihon Cornstarch corporation was used as cornstarch, Micropearl manufactured by Shimada Industry Co., Ltd. was used as rice starch, HPS101 manufactured by Freund Corporation was used as HPS (hydroxypropylstarch), and low-substituted hydroxypropylcellulose (LH-21 manufactured by Shin-Etsu Chemical Co., Ltd.) was used as L-HPC.

Examples 4-12

Preparation of Orally Rapidly Disintegrating Tablets

To the disintegrating particle composition prepared in Example 1 or 2 were added the ingredients of Table 2, 0.4 parts by weight of magnesium stearate, 0.2 parts by weight of aspartame and 0.2 parts by weight of menthol, and the mixture was combined, and then tableted by a rotary tableting machine as 50N of setting hardness to give a tablet with 240 mg of weight, 8 mm of diameter, and 9R (Examples 4-9 and 11-12).

To the disintegrating particle composition prepared in Example 3 were added the ingredients of Table 2 and 0.4 parts by weight of magnesium stearate, and the mixture was combined, and then tableted by a rotary tableting machine with 50N of setting hardness to give a tablet with 240 mg of weight, 8 mm of diameter, and 9R (Example 10).

Formulation

TABLE 2

|  | Disintegrating particle composition | Particle of Reference example 1 | Acetaminophen | HPS | Rice starch | Crospovidone | Crystalline cellulose | CMC |
|---|---|---|---|---|---|---|---|---|
| Example 4 | 61.2 (Example 1) | 25 |  |  | 10 | 3 |  |  |
| Example 5 | 54.2 (Example 1) | 25 |  | 7 | 10 | 3 |  |  |
| Example 6 | 54.2 (Example 1) | 25 |  | 7 | 7 | 5 |  |  |
| Example 7 | 63.7 (Example 2) | 25 |  | 7 |  | 3 | 0.5 |  |
| Example 8 | 61.4 (Example 2) | 25 |  | 7 |  | 5 | 0.8 |  |
| Example 9 | 58.2 (Example 2) | 25 |  | 10 |  | 5 | 1 |  |
| Example 10 | 59.6 (Example 3) | 10 |  |  |  | 20 |  | 10 |
| Example 11 | 39.2 (Example 2) |  | 30 |  |  | 20 | 10 |  |
| Example 12 | 64.2 (Example 2) |  | 30 |  |  | 5 |  |  |

(Unit: parts by weight)

CMC refers to carmellose.

Acetaminophen fine powder manufactured by Fuji Chemicals Ltd. was used as acetaminophen, carboxymethylcellulose NS-300 manufactured by Gotoku Chemical Company Ltd. was used as CMC, Kollidon CL manufactured by BASF Japan Ltd. was used as crospovidone, and Ceolus KG-802 manufactured by Asahi Kasei Chemicals Corporation was used as crystalline cellulose KG-802.

Comparative Example 1

78 Parts by weight of mannitol, 2 parts by weight of xylitol, 6 parts by weight of calcium silicate, and 14 parts by weight of cornstarch were mixed. 67.6 Parts by weight of the mixture, 25 parts by weight of the masking particles prepared in Reference example 1, 7 parts by weight of hydroxypropylstarch and 0.4 parts by weight of magnesium stearate were mixed. Since the resulted powders for tableting have low density and low fluidity, any setting tablets similar to the Examples could not be obtained due to the difficulty to load into a mortar although the resulted powders were tried to be tableted by a rotary tableting machine as 50N of setting hardness.

Comparative Example 2

78 Parts by weight of mannitol, 2 parts by weight of xylitol, 6 parts by weight of calcium silicate, and 14 parts by weight of cornstarch were put into a mortar, and thereto was added an appropriate amount of water. The mixture was kneaded, followed by filtering through 32 mesh sieve to granulate. The resultant was dried at 80° C. overnight. 67.6 Parts by weight of the mixture, 25 parts by weight of the masking particles prepared in Reference example 1, 7 parts by weight of hydroxypropylstarch and 0.4 parts by weight of magnesium stearate were mixed. Any setting tablets similar to the Examples could not be obtained due to the adherence and the broad weight variation of tablet, although the resulted powders were tried to be tableted by a rotary tableting machine as 50N of setting hardness.

Tableting Results

TABLE 3

|  | Molding pressure [kgf] | Tableting property | Hardness [N] | Disintegration time in the oral cavity [seconds] |
| --- | --- | --- | --- | --- |
| Comparative example 1 |  | difficult for tableting |  |  |
| Comparative example 2 |  | difficult for preparing tablet |  |  |
| Example 4 | 610-670 | good | 52.9 | 50 |
| Example 5 | 660-720 | good | 50.2 | 40 |
| Example 6 | 630-690 | good | 50.1 | 35 |
| Example 7 | 660-730 | good | 50.1 | 44 |
| Example 8 | 590-650 | good | 49.1 | 30 |
| Example 9 | 620-680 | good | 47.4 | 42 |
| Example 10 | 490-540 | good | 47.7 | 20 |
| Example 11 | 680-780 | good | 48.1 | 24 |
| Example 12 | 850-950 | good | 45.8 | 12 |

The tablets using the disintegrating particle compositions of Examples 4-12 had moderate molding pressure and hardness for use in tablet, and the disintegration time in the oral cavity was 60 seconds or below and the tablets had sufficient disintegrating properties in the oral cavity. It was difficult for tableting in the preparations of Comparative examples 1 and 2. It was difficult to prepare a tablet in the preparations of Comparative examples 1 and 2.

The invention claimed is:

1. A disintegrating particle composition, which is prepared by homogeneously dispersing inorganic excipient(s) and starch(es) in complex particles which are composed of mannitol and xylitol, wherein
   (a) the sum of mannitol and xylitol is 70 to 90 parts by weight;
   (b) the inorganic excipient(s) are in the amount of 2 to 15 parts by weight;
   (c) the starch(es) are in the amount of 5 to 25 parts by weight, and the total amount of the ingredients (a), (b) and (c) is 100 parts by weight,
       wherein the starch(es) are at least one selected from the group consisting of potato starch, flour starch, sticky rice starch, sweet potato starch, tapioca starch, rice starch, cornstarch and waxy cornstarch, and
       wherein the composition is obtained by a spraying method.

2. The composition of claim 1, wherein
   (a) the sum of mannitol and xylitol is 75 to 85 parts by weight;
   (b) the inorganic excipient(s) are in the amount of 3 to 9 parts by weight; and
   (c) the starch(es) are in the amount of 10 to 15 parts by weight.

3. The composition of claim 2, wherein the ratio by weight of mannitol to xylitol is 99:1 to 90:10.

4. The composition of claim 2, wherein the ratio by weight of mannitol to xylitol is 99:1 to 95:5.

5. The composition of claim 1, wherein the inorganic excipient(s) are at least one selected from the group consisting of magnesium aluminometasilicate, magnesium aluminosilicate, anhydrous silicic acid, calcium silicate, calcium hydrogen phosphate, calcium carbonate and talc.

6. A method for preparing the composition of claim 1, comprising a step wherein a dispersion comprising the ingredients (a) to (c) is spray-dried.

* * * * *